(12) United States Patent
Cho

(10) Patent No.: US 7,081,188 B1
(45) Date of Patent: Jul. 25, 2006

(54) ELECTRIC-CURRENT BIOSENSOR

(75) Inventor: Ching-Hsin Cho, Taipei (TW)

(73) Assignees: Biomedix Taiwan, Taipei (TW);
Biomedix, Inc., Fremont, CA (US)

( * ) Notice: Subject to any disclaimer, the term of this patent is extended or adjusted under 35 U.S.C. 154(b) by 0 days.

(21) Appl. No.: 11/033,636

(22) Filed: Jan. 13, 2005

(51) Int. Cl.
*G01N 27/327* (2006.01)

(52) U.S. Cl. .............................. 204/403.04; 204/403.02
(58) Field of Classification Search .............................. 204/403.01–403.15, 416–418
See application file for complete search history.

(56) References Cited

U.S. PATENT DOCUMENTS

| | | | |
|---|---|---|---|
| 6,299,757 B1 * | 10/2001 | Feldman et al. | 205/775 |
| 6,521,110 B1 * | 2/2003 | Hodges et al. | 204/403.14 |
| 6,923,894 B1 * | 8/2005 | Huang et al. | 204/403.06 |

* cited by examiner

*Primary Examiner*—Alex Noguerola
(74) *Attorney, Agent, or Firm*—Rosenberg, Klein & Lee

(57) ABSTRACT

An electric-current biosensor has first and second supports, a pair of positive and negative electrodes on the first supports, an activity area covers the positive and negative electrodes, a pair of testing ports on two sides of the second support, and an electrode film mating with the activity area. The pair of testing ports force the sample to flow into the activity area and stops the sample from flowing outside the support along the surface thereof.

19 Claims, 4 Drawing Sheets

ELECTRIC-CURRENT BIOSENSOR

BACKGROUND OF THE INVENTION

1. Field of the Invention

The present invention relates to an electric-current biosensor, and particularly to an electric-current biosensor that can be operated more easily to avoid the inconvenience of having to aim samples towards test holes, so that the samples can be guided more easily and effectively into the activity area for obtaining an accurate testing value.

2. Description of the Related Art

The simplest current method of determining blood glucose levels uses an electric-current biosensor, later applying the sample (such as blood) onto an electric-current biosensor. The electric-current biosensor allows an oxidation-reduction reaction to take place in the sample, thereby producing electric ions. The ions accumulate into an electric current on the electric-current biosensor. An electric-current biosensor is inserted into a measure meter for comparing and analyzing the current, thereby determining the blood glucose concentration.

Please refer to FIG. 3, which illustrates an electric-current biosensor of the prior art. The electric-current biosensor has an activity area 44 and conductive electrodes 46, which form the structure of a small contact area, thereby creating a small transient current. Without a sufficient current the measure meter cannot perform value comparing or analysis, and the measuring accuracy is affected.

Please refer to FIG. 4, which shows an improved electric-current biosensor of another prior art. The improved electric-current biosensor is designed to overcome the disadvantages caused by the small reaction area as seen in FIG. 3. The improved electric-current biosensor provides a larger electrode contacting area for obtaining an accurate reading. The biosensor has a support 48, which consists of a second support 52 covering a part of a first support 50. The first support 50 has a positive electrode 54, a negative electrode 56 and an activity area 58. The activity area 58 covers a portion of the positive electrode 54 and the negative electrode 56. The second support 52 has a circle testing port 60 and an electrode film 62. The testing port 60 corresponds to the activity area 58. The electrode film 62 is formed on the periphery around the testing port 60. When processing measurements, the first support 50 is covered by the second support 52 and the blood sample is applied onto the activity area 58. In this relative art the electrodes of the first support 50 and the second support 52 overlap each other to create a larger transient current, thereby improving the accuracy of the measure meter.

However, when the operator applies the blood sample into the testing port for measuring the blood glucose concentration, it requires strenuous effort to aim the sample accurately into the testing port. If this is not done properly, the sample will be forced outside the testing port by gravity, thereby wasting samples and sometimes resulting in medical personal having insufficient samples to test. Therefore the measure meter cannot achieve a sufficient measuring current quickly enough to perform value comparing and analyzing.

Although the related art raises the accuracy of blood glucose determination, the electric-current biosensor of the related art still has some inconveniences and disadvantages that can be improved upon. The inventor, after investigation and research, thus provides the present invention of logical design for improving the above-mentioned imperfections.

SUMMARY OF THE INVENTION

An objective of the present invention is to provide an electric-current biosensor that has a pair of testing ports formed on two sides thereof which is more convenient for users.

Another objective of the present invention is to provide an electric-current biosensor that is tilted slightly, therefore ensuring the sample will flow into the testing port to avoid wasting samples.

Another objective of the present invention is to provide an electric-current biosensor that increases the transient electric current and improves the accuracy of blood glucose testing.

In order to achieve the above objectives, the present invention provides an electric-current biosensor, which comprises a support, a pair of positive and negative electrodes, an activity area, and an electrode film. The support has a first support and a second support covered adhesively on the first support, wherein the second support is concaved with a pair of testing ports on two sides thereof. The pair of positive and negative electrodes is disposed on the first support. The pair of positive and negative electrodes are co-planar. The positive electrode has a positive electrode film and a positive conductive film. The negative electrode has a negative electrode film and a negative conductive film. The activity area is formed on the first support and is covered with the pair of positive and negative electrode films. The electrode film is formed on the second support and corresponds to the activity area. The electrode film is covered with the pair of positive and negative electrode films. The pair of testing ports mate with the activity area and are exposed outside a part of the activity area when the first support is covered by the second support.

BRIEF DESCRIPTION OF THE DRAWINGS

The invention will be better understood and objectives other than those set forth above will become apparent when consideration is given to the following detailed description thereof. The description makes reference to the attached drawings, wherein.

DESCRIPTION OF THE PREFERRED EMBODIMENT

Figure 1:
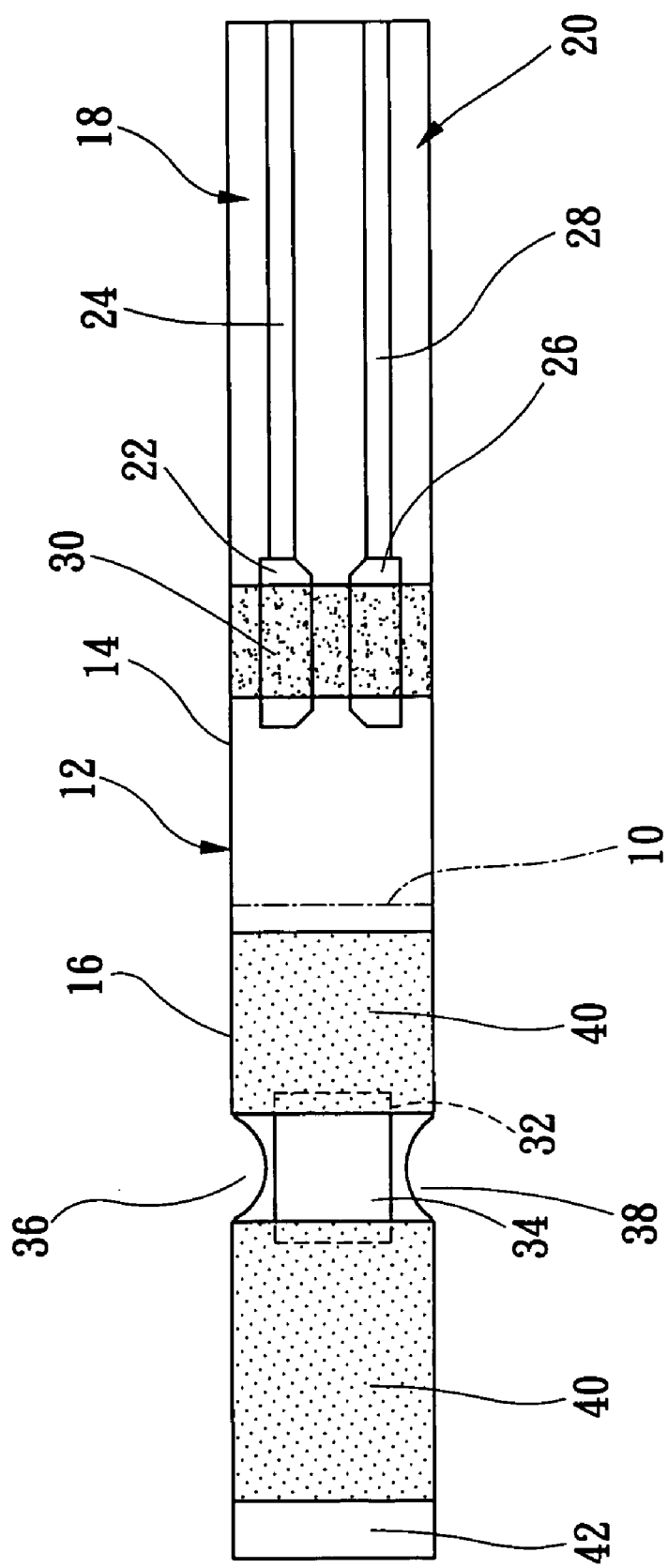
FIG. 1 is a top view of an unfolded electrical-current biosensor according to the present invention.

Please refer to the FIG. 1 in which the top view of an unfolded electrical-current biosensor according to the present invention is illustrated. The present invention provides an electric-current biosensor comprised of a support 10, a pair of positive and negative electrodes 18, 20, an activity area 30, and an electrode film 32.

The support 12 has a folding line 10 formed thereon to divide into a first support 14 and a second support 16. The first support 14 is longer than the second support 16. The folding line 10 is between the first support 14 and the second support 16 for folding and covering the second support 16 on the first support 14.

The first support 14 is formed with a positive electrode 18 and a negative electrode 20 which are coplanar. The positive electrode 18 and the negative electrode 20 are separated and do not overlap. The positive electrode 18 has a positive electrode film 22 and a positive conductive film 24. A unit of the positive electrode film 22 is larger than that of the positive conductive film 24. The negative electrode 20 has a negative electrode film 26 and a negative conductive film 28. A unit of the negative electrode film 26 is larger than that of the negative conductive film 28.

The activity area 30 is on the positive electrode film 22 and the negative electrode film 26. The composition of the activity area 30 accords to the item being measuring, the blood glucose, and consists of enzyme, enzyme protective agent, a conductive medium, surfactant, buffer solution, and water. Each composition is instanced as followed:

(1) Enzyme, such as glucose oxidase, etc.;

(2) Enzyme protective agent, such as albumin, dextrin, dextran, amino acid, etc.;

(3) A conductive medium, such as potassium, etc.;

(4) A surfactant, such as TritonX-100, TritonX-405, TritonX-114, sodium lauryl sulfate, polyoxyethylenesorbitan monolaurate (Tween 20), Tween 40, Tween 60, Tween 80, another water surfactant, or detergent;

(5) A buffer solution, i.e. slats, such as phosphate buffer solution, etc.; and

Water, such as distilled water.

The electrode film 32 is formed on the second support 16 and corresponds to the activity area 30. The electrode film 32 is covered with the pair of positive and negative electrode films 22 and 26. The electrode film 32 is applied to a mating activity area 34 by spreading. The mating activity area 34 has the same composition as the activity area 30.

The second support 16 is concaved with a pair of semi-circular testing ports 36 and 38 on two sides thereof, which correspond to the activity area 30. An adhesive layer 40 is disposed on the second support 16 to bond with the first and second supports 14 and 16 together. The adhesive layer 40 is disposed on two sides of the activity area 30, and does not cover the mating activity area 34, the testing ports 36 and 38 or a portion of the free end of the second support 16. The portion of the free end of the second support 16 is defined as an operating area 42. In this preferred embodiment, the adhesive layer 40 is a twin adhesive with a height of approximately 0.3 mm, which has an insulating base, so that the positive and negative electrodes 18 and 20 on the first support 14 do not cause a short circuit of the biosensor when the electrode film 32 on the second support 16 covers the first support 14.

Figure 2:
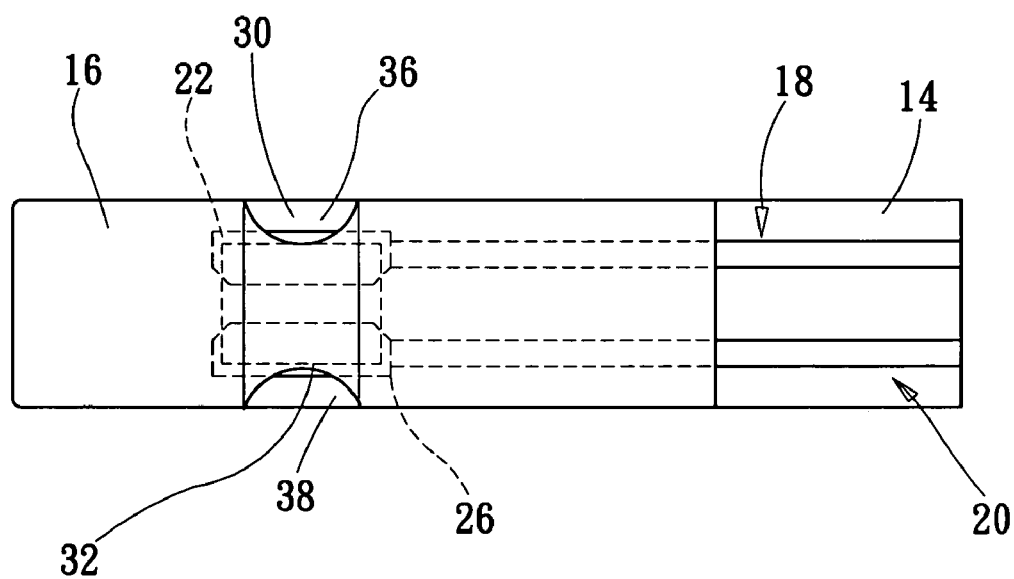
FIG. 2 is a top view of a folded electrical-current biosensor according to the present invention.
Figure 3:
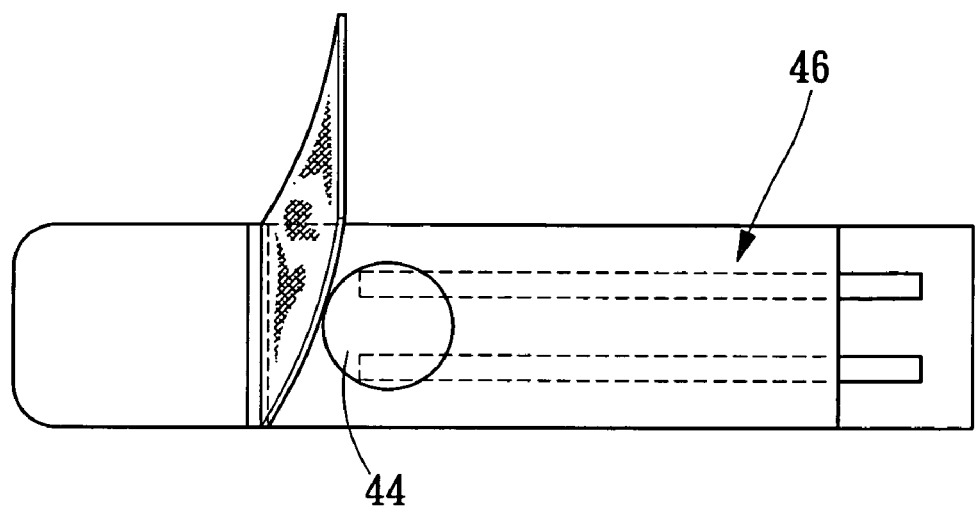
FIG. 3 is a top view of an unfolded electrical-current biosensor of a related art.
Figure 4:
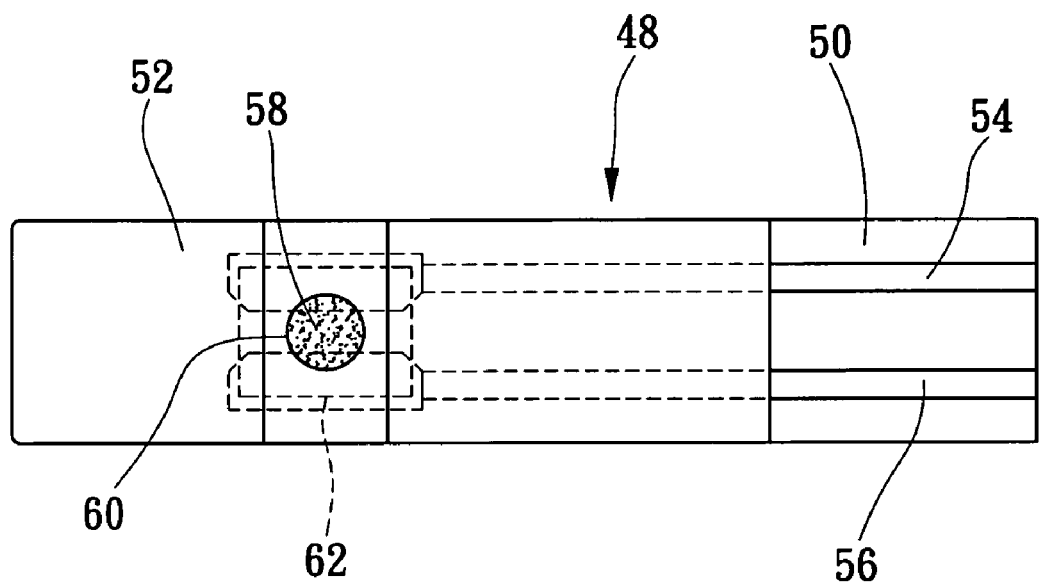
FIG. 4 is a side view of an unfolded electrical-current biosensor of another related art.

Referring to FIG. 2, when using the electric-current biosensor, the support 12 is folded along the folding line 10, and the second support 16 covers the first support 14. The pair of testing ports 36 and 38 of the second support 16 mate with the activity area 30 and are exposed outside a part of the activity area 30. The electrode film 32 overlaps above the positive electrode film 22 and the negative electrode film 26. The first and second supports 14 and 16 are joined together by the adhesive layer 40.

When measuring the blood glucose, the operator drops an appropriate amount of sample into one of the testing ports 36 or 38. The sample is then forced by gravity to flow into the activity area 30, it then diffuses and, because of the pressure, the sample oxidates within the activity area 30 quickly and produces electric ions. The electric ions move between the positive electrode 18 and the negative electrode 20. Finally the biosensor further cooperates with a measure meter to compare and analyze the current for determining the blood glucose concentration.

A summary of the characteristics and advantages of the electric-current biosensor, is as follows:

The present invention improves upon the disadvantages of the prior art. The circle testing port of the related art causes the sample to flow outside of the testing area, wasting samples and not providing accurate measurements. Especially when the sample is not applied properly in the testing port of the prior art, the sample will be pulled by gravity and will flow outside the support along the surface thereof because the biosensor is titled. The present invention forces the sample to flow into the activity area fully and raises the electrical current, thereby improving the accuracy of the measure meter.

Although the present invention has been described with reference to the preferred embodiments thereof, it will be understood that the invention is not limited to the details thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. An electric-current biosensor, comprising:
    a support including a first support and a second support, said second support being integrally connected to said first support along a folding line, wherein the second support includes a pair of testing ports formed at two sides thereof and extending exclusively through the thickness of said second support;
    a pair of positive and negative co-planar electrodes formed on the first support, the positive electrode having a positive electrode film and a positive conductive film, and the negative electrode having a negative electrode film and a negative conductive film;
    an activity area formed on the first support, said activity area covering a portion of the pair of positive and negative electrode films;
    a mating activity area formed at said second support between said testing ports;
    an electrode film formed on the second support between said testing ports; and
    a pair of adhesive portions formed at said second support in non-overlapping relationship in the said mating activity area;
    said electrode film being positioned in close proximity to said activity area as the result of folding said support along said folding line, and being maintained above the pair of positive and negative electrode films in overlapping relationship therewith by the adhesive connection of said pair of adhesive portions with said first support.

2. The electric-current biosensor as in claim 1, wherein the first support is longer than the second support.

3. The electric-current biosensor as in claim 1, wherein a unit area of the positive electrode film is larger than that of the positive conductive film.

4. The electric-current biosensor as in claim 1, wherein a unit area of the negative electrode film is larger than that of the negative conductive film.

5. The electric-current biosensor as in claim 1, wherein the electrode film on the second support is further applied with said mating activity area having the composition similar to the composition of the activity area.

6. The electric-current biosensor as in claim 1, wherein the adhesive portions are disposed at opposite sides of the activity area.

7. The electric-current biosensor as in claim 1, wherein the pair of adhesive portions is formed of a twin adhesive with a height of approximately 0.3 mm on an insulating base.

8. An electric-current biosensor, comprising:
a first support,
a second support integrally connected with the first support along a folding line, said secured support including a pair of testing ports at both sides thereof,
a pair of positive and negative electrodes formed on the first support, the positive electrode having a positive electrode film and a positive conductive film, and the negative electrode having a negative electrode film and a negative conductive film,
an activity area formed on the first support and covering a portion of the pair of positive and negative electrode films; and
an electrode film formed on the second support between the pair of testing ports, said electrode film being aligned with the activity area when said electric-current biosensor is folded along said folding line, wherein the pair of testing ports leaves parts of the activity area exposed when the first support covers the second support.

9. The electric-current biosensor as in claim 8, further comprising an adhesive layer disposed adjacently to the electrode film on the second support to adhere to the first support.

10. The electric-current biosensor as in claim 9, wherein the adhesive layer includes an approximately 0.3 mm double-sided adhesive tape provided with an insulating base.

11. The electric-current biosensor as in claim 8, wherein the first support is longer than the second support, and wherein another end of the second support is provided with an operating area.

12. The electric-current biosensor as in claim 8, wherein the activity area contains a composition including an enzyme, an enzyme protective agent, a conductive medium, a surfactant, a buffer solution, and water.

13. The electric-current biosensor as in claim 12, wherein the enzyme is glucose oxidase.

14. The electric-current biosensor as in claim 12, wherein the enzyme protective agent is selected from the group consisting of albumin, dextrin, dextran, and amino acid.

15. The electric-current biosensor as in claim 12, wherein the conductive medium is potassium.

16. The electric-current biosensor as in claim 12, wherein the surfactant is selected from the group consisting of TritonX-100, TritonX-405, TritonX-114, sodium lauryl sulfate, polyoxyethylenesorbitan monolaurate (Tween20), Tween40, Tween60, Tween80, water surfactant, and detergent.

17. The electric-current biosensor as in claim 12, wherein the buffer solution is phosphate buffer solution.

18. The electric-current biosensor as in claim 12, wherein the water is distilled water.

19. The electric-current biosensor as in claims 12, wherein the electrode film on the second support is applied with a composition similar to that of the activity area.

\* \* \* \* \*